(12) United States Patent
Sulser et al.

(10) Patent No.: US 9,115,157 B2
(45) Date of Patent: Aug. 25, 2015

(54) REGULATOR MOLECULE

(75) Inventors: Ueli Sulser, Unterengstringen (CH); Lukas Frunz, Zürich (CH); Jörg Zimmermann, Winterthur (CH)

(73) Assignee: SIKA TECHNOLOGY AG, Baar (CH)

( * ) Notice: Subject to any disclaimer, the term of this patent is extended or adjusted under 35 U.S.C. 154(b) by 285 days.

(21) Appl. No.: 13/806,218

(22) PCT Filed: Jul. 19, 2011

(86) PCT No.: PCT/EP2011/062345
§ 371 (c)(1),
(2), (4) Date: Dec. 21, 2012

(87) PCT Pub. No.: WO2012/010594
PCT Pub. Date: Jan. 26, 2012

(65) Prior Publication Data
US 2013/0109819 A1    May 2, 2013

(30) Foreign Application Priority Data

Jul. 21, 2010 (EP) .................... 10170324

(51) Int. Cl.
| C07F 9/30 | (2006.01) |
| C07F 9/50 | (2006.01) |
| C07F 9/32 | (2006.01) |
| C07F 9/572 | (2006.01) |
| C07F 9/59 | (2006.01) |
| C08K 5/5313 | (2006.01) |
| C08F 220/28 | (2006.01) |
| C07F 9/48 | (2006.01) |
| C07F 9/53 | (2006.01) |

(52) U.S. Cl.
CPC ............ C07F 9/3258 (2013.01); C07F 9/4816 (2013.01); C07F 9/5722 (2013.01); C07F 9/592 (2013.01); C08F 220/28 (2013.01); C08K 5/5313 (2013.01); *C07F 9/3264* (2013.01); *C07F 9/485* (2013.01); *C07F 9/4825* (2013.01); *C07F 9/5004* (2013.01); *C07F 9/5018* (2013.01); *C07F 9/5304* (2013.01)

(58) Field of Classification Search
CPC .... C07F 9/3258; C07F 9/3264; C07F 9/4825; C07F 9/485; C07F 9/5004; C07F 9/5304; C07F 9/5018; C07F 9/4816; C07F 9/5722; C07F 9/592; C08F 220/28; C08K 5/5313
USPC .................. 558/186, 108, 179, 70, 153, 183; 526/193, 274, 278
See application file for complete search history.

(56) References Cited

U.S. PATENT DOCUMENTS

| 2005/0227877 A1* | 10/2005 | Wo et al. ................ 508/345 |
| 2007/0021535 A1 | 1/2007 | Wursche et al. |
| 2009/0080079 A1 | 3/2009 | Kogure et al. |

FOREIGN PATENT DOCUMENTS

| EP | 1 731 559 A1 | 12/2006 |
| WO | WO 2006/050472 A2 | 5/2006 |

OTHER PUBLICATIONS

International Search Report issued in International Application No. PCT/EP2011/062345 dated Aug. 23, 2011 (w/translation).
International Preliminary Report on Patentability issued in PCT/EP2011/062345 dated Jan. 22, 2013.

* cited by examiner

Primary Examiner — Ling Choi
Assistant Examiner — David L Miller
(74) Attorney, Agent, or Firm — Oliff PLC

(57) ABSTRACT

The invention relates to a mono-substituted phosphinic acid and to the use thereof as a regulator in radical polymerization. Such regulators do not result in the formation of poorly soluble salts, and in addition, the polymers produced with the regulators according to the invention are characterized by a uniform polymerization degree having a narrow size distribution. In addition, the invention relates to a method for producing such mono-substituted phosphinic acids.

16 Claims, No Drawings

REGULATOR MOLECULE

TECHNICAL AREA

The invention relates to the area of producing polymers by free radical polymerization.

PRIOR ART

It is known that phosphinic acids and salts thereof may be used as molecular weight regulators, but there are drawbacks to their use. For example, when they are used, several unwanted and in some cases toxic byproducts are produced, for example phosphine at elevated temperatures; addition reactions sometimes do not proceed to completion, and in addition, they result in polymers with highly inhomogeneous degrees of polymerization.

In practice, sulfur-containing inorganic and organic compounds are used as molecular weight regulators, for example mercaptans, mercaptoethanol, thioglycol, mercaptopropionic acid, thiocarbamates and cysteine.

Sulfur-containing substances are disadvantageous because they are difficult to handle during polymerization and because their unpleasant odor, especially at higher temperatures, interferes with the production process and the utilization properties of products manufactured with these compounds.

In addition, the low-molecular-weight regulators used in the prior art up to now, such as phosphite or sulfite, have the drawback that the salts formed from the regulators during the reaction are of only limited solubility and therefore precipitate out from highly concentrated solutions.

SUMMARY OF THE INVENTION

Therefore it was the goal of the present invention to supply molecular weight regulators that do not have the drawbacks mentioned and can be used in free radical polymerizations.

Surprisingly it has now been found that a mono-substituted phosphinic acid of formula (I) according to claim 1 accomplishes this task. The use of the mono-substituted phosphinic acid according to the invention as a regulator in free radical polymerizations does not result in the formation of poorly soluble salts, and in addition, the polymers produced with the regulator according to the invention have a uniform degree of polymerization with a narrow size distribution.

In addition, a cost-advantageous and technically simple process for producing the mono-substituted phosphinic acids according to the invention in high yields was found.

Additional aspects of the invention form the subject matter of additional independent claims. Particularly preferred embodiments of the invention are the subject matter of dependent claims.

Methods of Executing the Invention

The present invention relates to mono-substituted phosphinic acids of the formula (I)

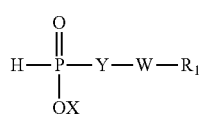

(I)

wherein X represents H⁺, an alkali metal ion, an alkaline earth metal ion, a divalent or trivalent metal ion, the ammonium ion, an organic ammonium group or an organic radical with a molecular weight of 5.200 g/mol; in particular, X represents Na⁺ or K.

Here, Y represents one of the formulas (II) to (VI)

(II)

(III)

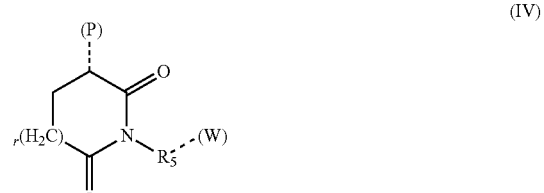

(IV)

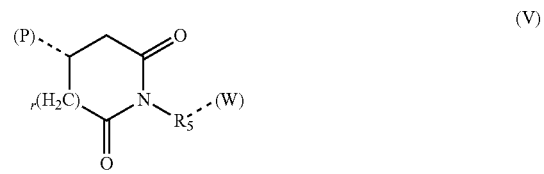

(V)

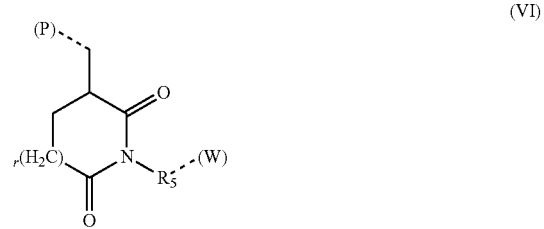

(VI)

and W represents one of the formulas (VII) to (X)

(VII)

(VIII)

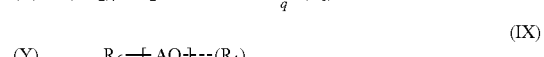

(IX)

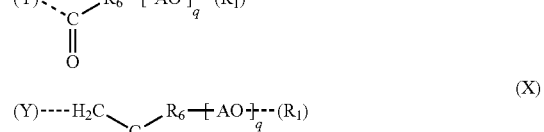

(X)

$R_1$ represents H, an alkyl group, preferably with 1-20 carbon atoms, an alkylaryl group, preferably with 7-20 carbon atoms, or the formula (XI)

(XI)

wherein the substituent A independently represents a $C_2$- to $C_4$-alkylene group, the subscript q represents a value from 2 to 300, in particular, of 2 to 50, particularly preferably from 3 to 10, the subscript n represents a value of 2 to 4, preferably a value of 2, and the subscript r represents a value of 0 to 1, wherein $R_2$, $R_3$ and $R_4$ independently represent H, $CH_3$, COOH or $CH_2$—COOH. It is clear to the person skilled in the art that in this connection, COOH or $CH_2$—COOH are also understood to include the salts thereof with alkali metal ions, alkaline earth metal ions, divalent or trivalent metal ions or ammonium ions, for example $COO^- Na^+$ or $CH_2$—$COO^- Na^+$.

$R_5$ represents —$CH_2$—$CH_2$— or —$CH_2$—$CH(CH_3)$— and $R_6$ represents O or N.

Preferably, [AO] represents the formula (XV)

 (XV)

The subscripts x, y, z each independently represent the values 0-300 and the sum thereof x+y+z is 2-300. In addition, in the formula (XV) EO=ethyleneoxy, PO=propyleneoxy, BuO=butyleneoxy or usobutyleneoxy. The sequence of the individual structural units EO-, PO-, and BuO may be alternating, stochastic, blockwise or random.

Preferably, the subscript x is from 2 to 50, particularly preferably from 3 to 15 and the sum y+z=0.

"Molecular weight" or "molar weight" is defined in the sense of the invention as the mean weight-average molecular weight Mw.

The term "polymer" in the present document comprises a population of macromolecules that on one hand are chemically uniform, but on the other hand differ in terms of degree of polymerization, molecular weight and chain length, produced by a polyreaction (polymerization, polyaddition, polycondensation). The term also includes derivatives of such a population of macromolecules from polyreactions, thus compounds obtained by reactions, for example additions or substitutions, of functional groups on pre-supplied macromolecules and which may be chemically uniform or chemically non-uniform.

The bold-face letters such as X, W, Y, Y', P, M and the like in the present document are intended merely for better reading comprehension and identification.

If X is an organic ammonium group, this is preferably an aliphatic amine or a hydroxyaliphatic amine, in particular, a mono-, di- or trialkylamine, for example methyl ether-, ethyl-, or diethylamine, or a mono-, di- or tri-(hydroxyalkyl)-amine, for example, ethanolamine, di- or triethanolamine, tris-(hydroxymethyl ether)methyl etheramine or N-(hydroxyethyl)-N,N-di-ethylamines.

If X is an organic radical with a molecular weight of ≤200 g/mol, it is preferably a $C_1$- to $C_{20}$-alkyl group or a radical containing alkylene oxide, with a molecular weight of ≤200 g/mol.

Preferably, the compound of formula (I)

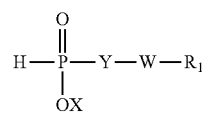 (I)

is a compound with
X=$H^+$ or $Na^+$
a W of formula (VII)
a Y of formula (III),
$R_1$=H or $CH_3$
$R_2$=$R_3$=$R_4$=H
wherein the subscripts are x=14-15 and y=z=0. or
a compound with
X=$H^+$ or $Na^+$
a W of formula (VII)
a Y of formula (III),
$R_1$=H or $CH_3$
$R_2$=$R_3$=$R_4$=H
wherein the subscripts are x=13-14 and y=0 and z=1. Or
a compound with
X=$H^+$ or $Na^+$
a W of formula (VIII)
a Y of formula (III),
$R_1$=H or $CH_3$
$R_2$=$R_3$=$R_4$=H
wherein the subscripts are x=2-8 and y=z=0. Or
a compound with
X=$H^+$ or $Na^+$
a W of formula (VIII)
a Y of formula (III),
$R_1$=H or $CH_3$
$R_2$=$R_3$=$R_4$=H
wherein the subscripts are x=3-10 and y=z=0. Or
a compound with
X=$H^+$ or $Na^+$
a W of formula (VIII)
a Y of formula (III),
$R_1$=H or $CH_3$
$R_2$=$R_3$=$R_4$=H
wherein the subscripts are x=9-11 and y=z=0. Or
a compound with
X=$H^+$ or $Na^+$
a W of formula (VIII)
a Y of formula (III),
$R_1$=H or $CH_3$
$R_2$=$R_3$=$R_4$=H
wherein the sum of the subscripts is x+y=20 and z=0. Or
a compound with
X=$H^+$ or $Na^+$
a W of formula (IX)
a Y of formula (III),
$R_1$=H or $CH_3$
$R_2$=H, $R_3$=H or $CH_3$, $R_4$=COON or $COO^-$ Na,
wherein the subscripts are x=2-8 and y=z=0.
Particularly preferably the compound of formula (I)

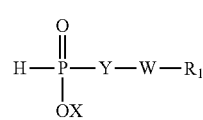 (I)

is a compound selected from the group consisting of:
Sodium[poly(oxyethylene)]-phosphinate, preferably with a molecular weight of 400-600 g/mol, sodium-2-[poly(oxyethylene)-1,4-dioxybutylene]ethylphosphinate, preferably with a molecular weight of 400-600 g/mol, sodium-3-[methyl-poly(oxyethylene)-oxy-]propylphosphinate (degree of alkoxylation: 2-8 EO), preferably with a molecular weight of 250-500 g/mol, sodium-3-[methyl-poly(oxyethylene)-oxy-]propylphosphinate (degree of alkoxylation: 3-10 EO), preferably with a molecular weight of 300-550 g/mol, sodium-3-[methyl-poly(oxyethylene)-oxy-]propylphosphinate (degree of alkoxylation: approx. 10 EO), preferably with a molecular weight of 500-600 g/mol, sodium-3-[methyl-poly(oxyethylene)-oxy-]propylphosphinate (degree of alkoxylation: approx. 24 EO), preferably with a molecular weight of 1100-1200 g/mol, sodium-3-[methyl-poly(oxyethyleneoxypropylene)-oxy-]propylphosphinate (degree of alkoxylation: approx. 20 EO and approx. 20 PO), preferably with a molecular weight of 1500-2200 g/mol.

In an additional aspect, the present invention relates to a process for producing a mono-substituted phosphinic acid by reacting a phosphinic acid of the formula (XII)

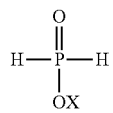
(XII)

with a compound of formula (XIII)

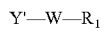
Y'—W—R$_1$    (XIII)

wherein Y' represents a compound of formula (III') to (VI')

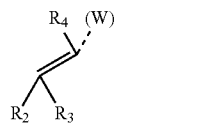
(III')

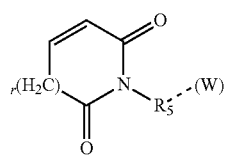
(IV')

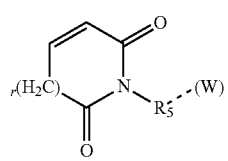
(V')

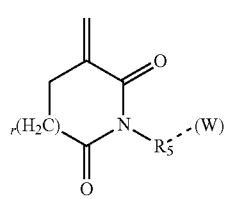
(VI')

and wherein W, $R_1$-$R_5$, X and r represent radicals or subscripts respectively, as were described in the preceding as radicals and subscripts respectively for W, $R_1$-$R_5$, X and r, in the presence of a free radical initiator.

Preferably, the reaction is a free radical addition reaction.
Preferably, the compound of formula (XIII)

Y'—W—R$_1$    (XIII)

is a compound with a Y' of formula (III'), a W of formula (VII) and $R_1$=$CH_3$, wherein $R_2$, $R_3$ and $R_4$ each independently represent H.

Particularly preferably it is methyl-poly(oxyethylene)vinyl ether, methyl-poly(oxypropylene)vinyl ether, or methyl-poly(oxyethyleneoxypropylene)-vinyl ether.

Particularly preferred are:
Poly(oxyethylene)-vinyl ether (degree of alkoxylation: 13-14 EO), with a molecular weight of approx. 500 g/mol, poly(oxyethylene)-1-oxytetramethyletherene-vinyl ether (degree of alkoxylation: 8-9 EO), with a molecular weight of approx. 500 g/mol.

Preferably, the compound of formula (XIII)

Y'—W—R$_1$    (XIII)

is a compound with a Y' of formula (III'), a W of formula (VIII) and $R_1$=$CH_3$, wherein $R_2$ and $R_3$ each independently represent H and $R_4$ represents H or $CH_3$.

In particular, this is preferably methyl-poly(oxyethylene) allyl ether, methyl-poly(oxypropylene)allyl ether, methyl-poly(oxyethyleneoxypropylene)allyl ether, methyl-poly(oxyethylene)methallyl ether, methyl-poly(oxypropylene)methallyl ether, methyl-poly(oxyethyleneoxypropylene) methallyl ether, methyl-poly(oxyethylene-oxypropylene) methyl etherbutene ether.

Particularly preferred are:
Poly(oxyethylene)-allyl methyl ether (degree of alkoxylation: 2-8 EO) with a molecular weight of approx. 250 g/mol, poly(oxyethylene)-allyl methyl ether (degree of alkoxylation: 3-10 EO) with a molecular weight of approx. 350 g/mol, poly(oxyethylene)-allyl methyl ether (degree of alkoxylation: 10 EO) with a molecular weight of approx. 500 g/mol, poly(oxyethylene)-allyl methyl ether (degree of alkoxylation: 24 EO) with a molecular weight of approx. 1100 g/mol, poly(oxyalkylene)-allyl methyl ether (degree of alkoxylation: 20 EO and 20 PO) with a molecular weight of approx. 2100 g/mol.

Preferably, the compound of formula (XIII)

Y'—W—R$_1$    (XIII)

is a compound with a Y' of the formula (III'), a W of formula (IX), and $R_1$=$CH_3$, wherein $R_2$ and $R_3$ independently represent H, $R_4$ is H or $CH_3$, and $R_6$ is 0.

Particularly preferably it is methyl-poly(oxyethylene) acrylate, methyl-poly(oxypropylene) acrylate, methyl-poly(oxyethyleneoxypropylene)acrylate, methyl-poly(oxyethylene)methacrylate, methyl-poly(oxypropylene)methacrylate, methyl-poly(oxyethyleneoxypropylene)methacrylate.

Preferably, the compound of formula (XIII)

Y'—W—R$_1$    (XIII)

is a compound with a Y' of formula (III'), a W of formula (IX), and $R_1$=$CH_3$, wherein $R_2$ and $R_3$ independently represent H, $CH_3$, $CH_2$—COOH or salts thereof, $R_4$ is H or $CH_3$ and $R_6$ is O.

Particularly preferably it is methyl-poly(oxyethylene) crotonate, methyl-poly(oxypropylene) crotonate, methyl-poly(oxyethyleneoxypropylene) crotonate, methyl-poly(oxyethylene) maleate, methyl-poly(oxypropylene) maleate, methyl-poly(oxyethyleneoxypropylene) maleate, methyl-poly(oxyethylene) fumarate, methyl-poly(oxypropylene)

fumarate, methyl-poly(oxyethyleneoxypropylene) fumarate, methyl-poly(oxyethylene) itaconate, methyl-poly(oxypropylene) itaconate, methyl-poly(oxyethylene-oxypropylene) itaconate, methyl-poly(oxyethylene) citraconate, methyl-poly (oxypropylene)-citraconate, methyl-poly (oxyethyleneoxypropylene) citraconate, methyl-poly (oxyethylene) aconitate, methyl-poly(oxypropylene) aconitate, methyl-poly(oxyethyleneoxypropylene)-aconitate.

Preferably, the compound of formula (XIII)

is a compound with a Y' of formula (III'), a W of formula (X), and $R_1$=$CH_3$, wherein $R_2$ is $CH_2$—COOH, $R_3$ and $R_4$ are H and $R_6$ is 0.

Particularly preferably it is methyl-poly(oxyethylene) pent-2-enedioic acid ester.

Preferably, the compound of formula (XIII)

is a compound with a Y' of formula (III'), a W of formula (IX), and $R_1$=$CH_3$, wherein $R_2$ and $R_3$ independently represent H, $CH_3$, or $CH_2$—COOH, $R_4$ is H or $CH_3$, and $R_6$ is N.

Particularly preferably it is N-[methyl-poly(oxyethylene)] maleic acid hemiamide, N-[methyl-poly(oxypropylene)]-maleic acid hemiamide, or N-[methyl-poly(oxyethyleneoxypropylene)]maleic acid hemiamide.

Preferably, the compound of formula (XIII)

is a compound with a Y' of formula (V'), a W of formula (VII), and $R_1$=$CH_3$, wherein $R_5$ is —$CH_2$—$CH_2$— or —$CH_2$—$CH(CH_3)$—$CH_2$, $R_6$ is N, and the subscript r=0.

Particularly preferably it is N-[methyl-poly(oxyethylene)] maleimide, N-[methyl-poly(oxypropylene)]maleimide, or N-[methyl-poly(oxyethyleneoxypropylene)]-maleimide.

Preferably, the phosphinic acid of formula (XII) is an alkali or alkaline earth salt or ammonium salt of phosphinic acid, in which one or more hydrogen atoms may be replaced by organic groups.

Such substituted ammonium compounds can be produced by neutralizing the phosphinic acid with amines or with C-hydroxylated aliphatic amines, in particular, mono-, di- or tri-lower alkyl amines, e.g., methyl ether-, ethyl-, or diethylamine, mono-, di- or tri-(hydroxy lower alkyl-amines, such as ethanolamine, di- or triethanolamine, tris-(hydroxymethyl ether) methyl ether amine or N-(hydroxy lower alkyl)-N,N-di-lower alkyl amines.

Particularly preferably the phosphinic acid of formula (XII) is sodium phosphinate monohydrate.

Preferred free radical initiators are peroxy acids and/or salts thereof, in particular, an ammonium or alkali metal salt of peroxodisulfuric acid. Particularly preferably, sodium peroxodisulfate is used as the free radical initiator.

The method preferably comprises the following steps:
a) a free radical addition reaction of the phosphinic acid of formula (XII) with a compound of formula (XIII) and a free radical initiator in a solvent;
b) optionally, removal of the solvent, in particular, by distillation, from the reaction mixture and optionally purification of the reaction product from the reaction mixture.

Preferably, the molar ratio of the compound of formula (XIII) to the phosphinic acid of formula (XII) is 1:1 to 1:10, preferably 1:2 to 1:6, particularly preferably 1:2 to 1:3. This is advantageous because of the higher yield of mono-substituted phosphinic acid.

Preferably, the method uses a solvent that is water or an aqueous solution of a solvent selected from the group consisting of ethanol, methanol, and isopropanol. Preferably, the solvent is water.

Water is preferred for financial and environmental reasons; also the use of water is safe in terms of manufacturing technology, and most salts are readily soluble in it.

It is also advantageous if the step a) is performed at a reaction temperature of 50° C. to 100° C., preferably of 60° C. to 80° C.

If the compound of formula (XIII) is a compound with a Y' of formula (III') and a W of formula (VII) or (VIII), it is advantageous for step a) to be performed at a pH of 4 to 8, preferably at a pH of 6 to 8.

It is also advantageous to perform purification in step b) with an extraction agent selected from the group consisting of ethanol, isopropanol, n-propanol, isobutanol, n-butanol, ethylene glycol monomethyl ether, and ethylene glycol dimethyl ether. Preferably, the extraction agent is isopropanol.

In a preferred embodiment in step a) an aqueous solution of sodium phosphinate is taken initially and then, preferably within 60-300 min, an aqueous solution of a compound of formula (XIII) with a Y' of formula (III') and a W of formula (VII) or (VIII) together with the free radical initiator is added dropwise. The temperature during the reaction in step a) is preferably 60-80° C.

Preferably, the molar ratio of sodium phosphinate to the compound of formula (XIII) is 1:1 to 1:10, particularly preferably 1:2 to 1:6.

Preferably, the molar ratio of free radical initiator to the compound of formula (XIII) is 0.005:1 to 0.2:1, particularly preferably 0.01:1 to 0.05:1.

It may further be advantageous in step b) to remove the solvent by evaporating the reaction solution to dryness. Also advantageous is purification of the reaction product in the reaction mixture. For this purpose the residue is agitated for 30-60 min in an extraction agent in which the reaction product is soluble, wherein after filtration the inorganic salts remain as a filter cake. Then a crude reaction product is obtained from the filtrate by evaporation.

The excess phosphinate can be recovered from the filter cake by recycling and made available for reuse.

Additional preferred embodiments are methods with the following reactions:

Sodium phosphinate with methyl-poly(oxyethylene)acrylate (degree of alkoxylation: 3-8 EO), or sodium phosphinate with methyl-poly(oxyethylene) maleate (degree of alkoxylation: 11 EO), or sodium phosphinate with N-[methyl-poly (oxyethylene)-maleic acid hemiamide (degree of alkoxylation: 13 EO), or sodium phosphinate with N-[methyl-poly (oxyethylene)]maleimide (degree of alkoxylation: 13 EO).

An additional aspect of the invention relates to the use of a mono-substituted phosphinic acid of formula (I), as described in the preceding, and the use of a mono-substituted phosphinic acid, produced by reacting a phosphinic acid of formula (XII) with a compound of formula (XIII), as described in the preceding, as molecular weight regulators in free radical polymerizations.

In the present document, the term "molecular weight regulators" is used to designate a compound with high transfer constants that are used in free radical polymerizations. Molecular weight regulators accelerate chain termination reactions and thus cause a reduction in the degree of polymerization of the resulting polymer without affecting the overall reaction rate.

In an additional aspect, the invention relates to a process for producing polymers P by free radical polymerization of monomers M using a mono-substituted phosphinic acid of formula (I) or a mono-substituted phosphinic acid produced by reacting a phosphinic acid of formula (XII) with a compound of formula (XIII), as described in the preceding.

It is also possible, in addition to a mono-substituted phosphinic acid named in the preceding, to use additional conventional molecular weight regulators, for example organic thiols. The molecular weight regulators according to the invention can be added simultaneously with other reaction components, bur also at different times. The addition of the molecular weight regulators is preferably performed continuously in the course of the polymerization reaction or by placing in the reactor in advance.

Preferably, the monomers M are selected from the group consisting of:
monoethylenically unsaturated ($C_3$-$C_6$)-mono- and dicarboxylic acids,
($C_1$-$C_{20}$)-(meth-)alkyl acrylates, ($C_1$-$C_{20}$)-(meth-)alkyl acrylamides, ($C_1$-$C_{20}$)-(meth-)alkyl acrylonitriles and poly(oxyalkylene)(meth-)acrylates,
vinyl esters of carboxylic acids containing 2 to 20 C atoms, vinylaromatics with to 20 C atoms,
vinyl ethers and allyl ethers of alcohols containing 1-12 C-atoms, methyl-poly(oxyalkylene)-allyl ethers, methyl-poly(oxyalkylene) vinyl ethers,
aliphatic hydrocarbons with 2-10 C atoms and 1 or 2 olefinic double bonds, cyclic and open-chain N-vinylamides,
and mixtures of these monomers.

Preferred monoethylenically unsaturated ($C_3$-$C_6$)-mono- and dicarboxylic acids are, for example, acrylic acid, methacrylic acid, vinylacetic acid, crotonic acid, fumaric acid, maleic acid, itaconic acid and their $C_1$-$C_{20}$-alkyl esters and methyl-poly(oxyalkylene)esters, their amides, nitriles and anhydrides.

The following may be mentioned as examples: methyl acrylates, ethyl acrylates, methyl methacrylates, ethyl methacrylates, 2-ethylhexyl acrylate, 2-ethylhexyl methacrylate, methyl-poly(oxyethylene) acrylate, methyl-poly(oxypropylene) acrylate, methyl-poly(oxyethyleneoxypropylene) acrylate, methyl-poly(oxyethylene) methaycrylate [sic], methyl-poly(oxypropylene) methacrylate, methyl-poly(oxyethyleneoxypropylene) methacrylate, maleic anhydride, itaconic acid anhydride, monomethyl maleate, dimethyl maleate, monoethyl maleate, diethyl maleate, mono-[methyl-poly(oxyethylene)]maleate, mono-[methyl-poly(oxypropylene)]maleate, mono-[methyl-poly(oxyethyleneoxypropylene)]maleate, di-[methyl-poly(oxyethylene)]maleate, di-[methyl-poly(oxypropylene)]maleate, di-[methyl-poly(oxyethyleneoxypropylene)]maleate, alkylene glycol acrylates and methacrylates, alkylene glycol maleates and itaconates, acrylamide, methycrylamide [sic], N,N-dimethyl acrylamide, and dialkylaminoalkylacrylamides and -methaycrylamides[sic].

As ($C_1$-$C_{20}$)-(meth-)alkyl acrylates, ($C_1$-$C_{20}$)-(meth-)alkyl acrylamides, ($C_1$-$C_{20}$)-(meth-)alkylacrylonitriles and poly(oxyalkylene)(meth-) acrylates are preferred:
($C_1$-$C_{10}$)-hydroxyalkyl acrylates and -methacrylates such as hydroxyethyl acrylate, hydroxypropyl acrylate, hydroxybutyl acrylate, hydroxyethylmethacrylate, hydroxypropyl methycrylate [sic], hydroxyisobutmethacrylate Preferred vinyl monomers are, for example, vinyl acetate, vinyl propionate, vinyl laurate, vinyl stearate, Versatic acid vinyl ester and N-vinylpyrrolidone.

Preferred vinylaromatic compounds are o- and p-methylstyrene, vinyltoluene and particularly preferably styrene.

Preferred vinyl ethers that may be mentioned are, for example, methyl vinyl ether, ethyl vinyl ether, butyl vinyl ether, 4-hydroxybutyl vinyl ether, isopropyl vinyl ether, propyl vinyl ether, vinyl isobutyl ether and dodecyl vinyl ether.

Particularly preferred vinyl monomers are the vinyl ethers of the methyl-polyalkylene glycols such as methyl-poly(oxyethylene) vinyl ether (degree of alkoxylation: 2-24 EO), methyl-poly(oxypropylene) vinyl ether (degree of alkoxylation: 2-20 EO) and methyl-poly(oxyethyleneoxypropylene) vinyl ether with variable EO:PO ratios.

However, open-chain N-vinylamide compounds such as N-vinylformamide, N-vinyl-N-methylformamide, N-vinylacetamide, and N-vinyl-N-methylacetamide may also be used.

Additional preferred monomers are, for example, ($C_1$-$C_{10}$)-alkylallyl ethers, and very particularly preferred are the poly(oxyalkylene)allyl ethers and the methyl-poly(oxyalkylene)allyl ethers, which may have different degrees of alkoxylation. The following may be mentioned as examples: poly (oxyethylene) allyl ethers, poly(oxypropylene) allyl ethers, poly(oxyethyleneoxypropylene) allyl ethers with variable EO:PO-ratios, methyl-poly(oxyethylene) allyl ethers, methyl-poly-(oxypropylene) allyl ethers and methyl-poly (oxyethyleneoxypropylene) allyl ethers with variable EO:PO ratios.

Examples of aliphatic hydrocarbons with 2-8 C atoms and one or two olefinic double bonds are ethylene, propylene, 1-butene, isobutene, and isoprene.

In addition, all other ethylenically unsaturated monomers, the polymerization of which proceeds according to a free radical-initiated mechanism, are possible.

Preferably, the free radical polymerization is performed in emulsion, in bulk, or in solution, preferably in solution; in particular, preferably in water. The free radical polymerization can be performed in the manner known to a person skilled in the art, typically in a polymerization reactor that is equipped with an agitator, several inflow vessels and lines, reflux condensers, heating and cooling devices, and is suitable for working under an inert gas atmosphere and at pressures above or below atmospheric pressure.

The choice of the various oxyalkyl groups in the $[(EO)_x$—$(PO)_y$-$(BuO)_z]$ of formula (XV) in [AO] of W of compound (I) makes systematic control of the solution behavior of the molecular weight regulator in the system possible.

In polymerization reactions that are performed in organic solvents or as emulsion polymerization, preferably regulators with hydrophobic groups in excess are used, e.g., PO or BuO groups, individually or in combination, with a small fraction, in particular, ≤30 wt.-%, preferably ≤20 wt.-%, particularly preferably ≤10 wt.-%, EO groups, based on the molecular weight of the mono-substituted phosphinic acid.

By the introduction of ≥50 wt.-%, especially of exclusively EO groups in [AO] of W of compound (I), the molecular weight regulators achieve a hydrophilic solubility behavior, so that these molecular weight regulators are preferably used for solution polymerizations in aqueous media.

It is also advantageous if the free radical polymerization is performed in the presence of at least one organic solvent and the mono-substituted phosphinic acid has a fraction of ≥70 wt.-%, preferably ≥80 wt.-%, oxypropyl groups (PO) or oxybutyl groups (BO), based on the molecular weight of the mono-substituted phosphinic acid, wherein the fraction of the organic solvent is 5-90 wt.-%, preferably 5-50 wt.-%, based on the total weight of the solvent.

This is advantageous in that as a result, the solubility of the mono-substituted phosphinic acid in the solvent is improved and the mono-substituted phosphinic acid scarcely precipitates, or particularly preferably does not precipitate at all, which is advantageous for the production process.

The term "organic solvent" in the present document is applied to compounds listed as organic solvents in CD Römpp Chemie Lexikon, 9th Edition, version 1.0, Georg Thieme Verlag, Stuttgart 1995.

It is further advantageous if the free radical polymerization is performed in the presence of water and the mono-substituted phosphinic acid has a fraction of 50 wt.-%, preferably ≥70 wt.-%, particularly preferably ≥80 wt.-%, ethylene groups (EO), based on the molecular weight of the mono-substituted phosphinic acid, wherein the fraction of water is 50-100 wt.-%, based on the total weight of the solvent.

This is advantageous in that as a result the solubility of the mono-substituted phosphinic acid in water is improved, and the mono-substituted phosphinic acid scarcely precipitates, or particularly preferably does not precipitate at all, which is advantageous for the production process.

It is also advantageous if the free radical polymerization has a free radical initiator selected from the group consisting of:
Peroxodisulfates such as sodium, potassium or ammonium peroxodisulfate;
2,2'-Azobis-isobutyronitrile;
and redox systems on the basis of hydroperoxides such as hydrogen peroxide, t-butylhydroperoxide, cumene hydroperoxide, which are used alone or together with redox initiators, for example, sodium bisulfite, sodium sulfite, ascorbic acid, isoascorbic acid and sodium formaldehyde sulfoxylate.

The term "free radical initiator" in the present document designates a compound such as is described as an initiator in CD Römpp Chemie Lexikon, 9th Edition, Version 1.0, Georg Thieme Verlag, Stuttgart 1995, suitable for free radical polymerizations.

Preferably, the free radical initiator is used in a proportion of 0.05 to 20 wt.-%, preferably 0.01 to 10 wt.-%, particularly preferably in a proportion of 0.1 to 2 wt.-%, based on the total weight of the monomer M.

If the reaction is performed in water, preferably initiators are used that are readily soluble in water. Particularly preferred are peroxodisulfates such as sodium, potassium or ammonium peroxodisulfate, but also 2,2'-azobis-isobutyronitrile or redox systems on the basis of hydroperoxides such as hydrogen peroxide, t-butyl hydroperoxide, [or] cumene hydroperoxide, which are used alone or in combination with redox initiators, for example, sodium bisulfite, sodium sulfite, ascorbic acid, isoascorbic acid and sodium formaldehyde sulfoxylate.

The free radical initiator can be added to the reactor in various ways over the course of the free radical polymerization. It can be added to the polymerization vessel all at once or added as it is consumed during polymerization, continuously or stepwise. Specifically, this depends on the polymerization temperature and on the chemical properties of the initiator system. Preferably, a small portion of the initiator is usually taken initially, and the remainder added to the polymerization mixture as it is consumed. It is frequently advisable to perform the polymerization reaction so that first 40-50 wt.-% of the free radical initiator is added continuously over a longer time period and then 50-60 wt.-% of the free radical initiator is added to the polymerization reactor over a shorter time period.

The polymerization temperatures depend on the degradation constants and normally fall in the range of 50-120° C., preferably 60-80° C., particularly preferably 80-100° C.

Advantageously, the mol-% ratio of the mono-substituted phosphinic acid or the salt thereof to the monomers M used in the free radical polymerization is 0.1-20, preferably 1-5, based on the total molar amount of the mono-substituted phosphinic acid and monomers M used in the free radical polymerization.

Preferably, the free radical initiator is used in a ratio of 0.001 to 10 wt.-%, preferably 0.05 to 5 wt.-%, particularly preferably in a ratio of 0.1 to 2 wt.-%, based on the total weight of the monomers M used.

It is also possible to place a small portion, about 5-10 wt.-%, of the total quantity of the molecular weight regulator in the reactor in advance, together with a small weight fraction, about 5 to 10 wt.-%, of the total free radical initiator quantity, and then add the reaction components simultaneously through separate inlets, i.e., the addition of the molecular weight regulators is performed in parallel to the monomer addition, wherein the quantities are selected such that preferably most of the molecular weight regulator is added during the same time period in which the monomers are also added.

In additional preferred embodiments, the addition of the molecular weight regulator takes place through operating methods in which the addition of the molecular weight regulator is done before the monomer inflow is started.

It is also advantageous if the polymers P produced by the free radical polymerization have a molecular weight of 500-200.000 g/mol, preferably 2.000-50.000 g/mol.

An additional aspect of the invention relates to a polymer of formula (XIV)

(XIV)

wherein X, Y, W, and $R_1$ represent radicals as described in the preceding;
and $R_7$ represents a polymer containing at least one monomer M as described in the preceding, in the polymerized state, wherein $R_7$ has a molecular weight of 500-200.000 g/mol, preferably 2.000-50.000 g/mol.

Preferably, $R_7$ consists of 80 wt.-%, in particular, 90 wt.-%, particularly preferably ≥95 wt.-%, of monomers M in their polymerized state, based on the molecular weight of $R_7$.

Monomers NI in their polymerized state are defined as monomers M which, after a free radical polymerization reaction, exist in the form of a polymer.

EXAMPLES

Description of the Measurement Methods

The infrared spectra were measured on an FT-IR 1600 device from Perkin-Elmer (horizontal ATR measurement unit with ZnSe crystals); the samples were applied undiluted as films. The absorption bands are reported in wave numbers (cm$^{-1}$) (measurement window: 4000-650 cm$^{-1}$).

$^1$H-NMR spectra were measured on a Bruker Model DPX-300 spectrometer at 300.13 MHz; the chemical shifts ☐ are reported in ppm. The coupling patterns (t, m) were reported even if they were only pseudo-coupling patterns.

$^{31}$P-NMR spectra were measured on a Bruker Model DPX-300 spectrometer at 300.13 MHz using CDCl$_3$ as the solvent.

The viscosity was measured on a Mettler Toledo Model RM 180 rotational viscometer (measurement system 11, cylinder 1, density 1.1, interval 100, rotation speed 100 rpm).

The chromatographic measurements were taken with an ACQUITY UPLC® from the Waters Corporation using an ELS and a PDA detector and a BEH 300 C18, 2.1×100 mm, 1.7 μm column with 0.15% HCOOH in water as solvent system A and acetonitrile as solvent system B.

Production of compounds of formula (I)

Example 1

Sodium-3-[methyl-poly(oxyethylene)-oxy-]propyl phosphinate (degree of alkoxylation: 3-10 EO, Mw 400-600 g/mol)

In a glass reactor with mechanical agitator, thermometer and dropping funnel, 106 g (1 mol) sodium hypophosphite monohydrate, dissolved in 300 g water, were placed and heated to 70° C. Then to this solution was added dropwise at 70-72° C. over 90 min a solution of 70 g (approx. 0.2 mol) (poly(oxyethylene)-allyl methyl ether (degree of alkoxylation: 3-10 EO) and 1 g sodium peroxodisulfate in 100 g water.

Then the reaction was continued for an additional 30 min at 70° C. until no further allyl methyl ether could be detected in the gas chromatogram. Next the reaction solution was evaporated to dryness. The residue was taken up in 350 g isopropanol and this slurry was agitated for 30 min at room temperature and then filtered over a glass filter funnel.

The filter cake, mostly consisting of excess sodium hypophosphite, was washed with 50 mL isopropanol and then dried over 50 g anhydrous sodium sulfate. The dried filtrate was filtered through a pleated filter and evaporated to dryness. The result was 70 g of crude product. For further purification, the highly hygroscopic crude product was dried for two hours under a high vacuum and then dissolved in 100 g isopropanol and filtered through a 10 μm filter. The filtrate was evaporated to dryness and the colorless residue was dried overnight under a high vacuum. 68.5 g (78.2%) of a colorless, waxy, chromatographically pure (UPLC) product was obtained.

Analysis

| | |
|---|---|
| Molecular weight (theoretical) | 454 g/mol |
| Elemental analysis calculated (%): | C 45.92, H 8.15, P 6.83 |
| Elemental analysis found (%): | C 42.54, H 7.68, P 7.88 |
| IR (Film): | 2289 cm$^{-1}$(P—H), 1296 cm$^{-1}$(P=O), 1098 cm$^{-1}$(C—O—C) |
| H-NMR (CDCl$_3$): | δ 8.00-5.90 ppm (m, 1H, P—H); 3.90-3.41 ppm (m, CH$_2$—O); 1.85-1.45 ppm (m, 4H, CH$_2$—CH$_2$) |
| $^{31}$P-NMR: | Δ (ppm): 47.05; 33.37; 29.11; 25.11. |
| MS: | 315 {[MH]$^+$, n = 4 mol EO}; 359 {[MH]$^+$, n = 5}; 403 {[MH]$^+$, n = 6}; 447 {[MH]$^+$, n = 7} 491 {[MH]$^+$, n = 8}; 535 {[MH]$^+$, n = 9}; 579 {[MH]$^+$ n = 10}; 623 {[MH]$^+$, n = 11}, 667 {[MH]$^+$, n = 12}; 711 {[MH]$^+$, n = 13}; 755 {[MH]$^+$, n = 14}; |

Example 2

Sodium-3-[methyl-poly(oxyethylene)-oxy-]propyl phosphinate (degree of alkoxylation: 2-8 EO, Mw=250-400 g/mol)

In a 2-liter glass reactor with a mechanical agitator, thermometer and dropping funnel, 212 g (2 mol) sodium hypophosphite monohydrate, dissolved in 600 g water, were placed and heated to 70° C. Then to this solution at 70-72° C. over 90 min was added dropwise a solution of 100 g (approx. 0.4 mol) poly-(oxyethylene)-allylmethyl ether (degree of alkoxylation: 2-8 EO) and 2 g (0.008 mol) sodium peroxodisulfate in 100 g water.

Then agitation was continued for an additional 30 min at 70° C. until no further allyl ether could be detected by liquid chromatography, and then the reaction solution was evaporated to dryness on a rotary evaporator. The residue was taken up in 600 g isopropanol and this slurry was agitated for 30 min. at room temperature and then filtered over a filter funnel.

The filter cake, consisting primarily of excess sodium hypophosphite, was now washed with 80 mL isopropanol and the filtrate dried over 75 g anhydrous sodium sulfate.

The dried filtrate was filtered through a pleated filter and evaporated to dryness. 112.4 g crude product was obtained.

For further purification the highly hygroscopic crude product was dried for two hours under high vacuum and then dissolved in 150 g isopropanol and filtered through a 10 μm filter. The filtrate was evaporated to dryness and the colorless residue dried overnight under high vacuum. 109.1 g (81.2%) of a colorless, waxy, chromatographically (UPLC) pure product was obtained.

Example 3

Sodium-3-[methyl-poly(oxyethylene)-oxy-]propyl phosphinate (degree of alkoxylation: approx. 10 EO, Mw=500-600 g/mol)

In a glass reactor with mechanical agitator, thermometer and dropping funnel, 106 g (1 mol) sodium hypophosphite monohydrate, dissolved in 300 g water, were placed and heated to 70° C.

Then to this solution was added dropwise at 75-76° C. over 120 min a solution of 100 g (approx. 0.2 mol) of methyl-poly (oxyethylene)allyl methyl ether (degree of alkoxylation: approx. 10 EO) and 1.2 g sodium peroxodisulfate in 100 g water. Then the reaction was continued for an additional 45 min at 75° C. until poly(oxyethylene)-allyl methyl ether sulfate was no longer detectable by liquid chromatography. Then the reaction solution was evaporated to dryness. The residue was taken up in 400 g isopropanol and this slurry was agitated for 30 min at room temperature and filtered over a filter funnel.

The filter cake, which mainly consisted of excess sodium hypophosphite, was now washed with 75 mL isopropanol and the filtrate dried over 80 g anhydrous sodium sulfate. The dried filtrate was filtered through a pleated filter and evaporated to dryness. 92 g crude product was obtained. For further purification, the highly hygroscopic crude product was dried for two hours under high vacuum and then dissolved in 150 g isopropanol and filtered through a 10 μm filter.

The filtrate was evaporated to dryness and the colorless residue was dried overnight under high vacuum. 88.5 g (75.3%) of a colorless, waxy, chromatographically (UPLC) pure product was obtained.

Example 4

Sodium-3-[methyl-poly(oxyethylene)-oxy-]propyl phosphinate (degree of alkoxylation: approx. 24 EO, Mw=1100-1200 g/mol)

In a glass reactor with mechanical agitator, thermometer and dropping funnel, 106 g (1 mol) sodium hypophosphite monohydrate, dissolved in 300 g water, were placed and heated to 75° C. Then to this solution was added dropwise at 75-76° C. over 160 min a solution of 220 g (approx. 0.2 mol)

poly(oxyethylene)-allyl methyl ether (degree of alkoxylation: approx. 24 EO) and 1.2 g sodium peroxodisulfate in 230 g water. The reaction was continued for an additional 45 min at 75° C. until no further allyl ether could be detected by liquid chromatography, and then the reaction solution was evaporated to dryness on a rotary evaporator. The residue was taken up in 800 g isopropanol, and this slurry was agitated for 30 min at room temperature and then filtered over a filter funnel. The filter cake, mostly consisting of excess sodium hypophosphite, was now washed with 300 mL isopropanol and the filtrate dried over 120 g anhydrous sodium sulfate. The dried filtrate was filtered through a pleated filter and evaporated to dryness. 195 g crude product was obtained.

For further purification, the highly hygroscopic crude product was dried for two hours under high vacuum and then dissolved in 200 g isopropanol and filtered through a 10 μm filter. The filtrate was evaporated to dryness and the colorless residue dried overnight under high vacuum. 171 g (72%) of a colorless, waxy, chromatographically (UPLC) pure product was obtained.

Example 5

Sodium-3-[methyl-poly(oxyethyleneoxypropylene)-oxy-]propyl-phosphinate (degree of alkoxylation: approx. 20 EO and 20 PO, Mw=1500-2200 g/mol)

In a glass reactor with mechanical agitator, thermometer and dropping funnel, 106 g (1 mol) sodium hypophosphite monohydrate, dissolved in 300 g water, were placed and heated to 75° C. Then to this solution was added dropwise at 75-76° C. over 160 min a solution of 420 g (approx. 0.2 mol) poly(oxyethylene-oxypropylene)-allyl methyl ether (degree of alkoxylation: approx. 20 EO and 20 PO) and 1.2 g sodium peroxodisulfate in 800 g water/ethanol (1:1). Then the reaction was continued for an additional 60 min at 75° C. until no further allyl methyl ether could be detected by liquid chromatography. Then the reaction solution was evaporated to dryness on a rotary evaporator. The residue was taken up in 900 g isopropanol and this slurry was agitated for 30 min at room temperature and then filtered over a filter funnel. The filter cake, mostly consisting of excess sodium hypophosphite, was now washed with 300 mL isopropanol and the combined filtrates dried over 120 ganhydrous sodium sulfate. The dried filtrate was filtered through a pleated filter and evaporated to dryness. 386 g crude product was obtained.

For further purification the hygroscopic crude product was dried for two hours under high vacuum and then dissolved in 500 g isopropanol and filtered through a 10 μm filter. The filtrate was evaporated to dryness and the colorless residue dried overnight under high vacuum. 355 g (81%) of a light yellow, waxy, chromatographically (UPLC) pure product was obtained.

Example 6

Sodium[poly(oxyethylene)]-phosphinate (degree of alkoxylation: 13-14 EO, Mw=500-700 g/mol)

In a glass reactor with mechanical agitator, thermometer and dropping funnel, 212 g (2 mol) sodium hypophosphite monohydrate, dissolved in 600 g water, was placed and heated to 70° C. Then to this solution was added dropwise at 70-72° C. over 90 min a solution of 200 g (approx. 0.4 mol) poly(oxyethylene)-vinyl ether of molecular weight approx. 500 g/mol and 2.3 g (0.01 mol) sodium peroxodisulfate in 100 g water. Then the reaction was continued for an additional 30 min at 70° C. until vinyl ether was no longer detectable by liquid chromatography, and then the reaction solution was evaporated to dryness on a rotary evaporator.

The residue was taken up in 600 g isopropanol; this slurry was agitated for 30 minutes at room temperature and then filtered over a filter funnel. The filter cake, mainly consisting of excess sodium hypophosphite, was now washed with 80 mL isopropanol and the combined filtrates dried over 75 g anhydrous sodium sulfate. The dried filtrate was filtered through a pleated filter and evaporated to dryness. 191.4 g crude product was obtained.

For further purification, the highly hygroscopic crude product was dried for two hours under high vacuum and then dissolved in 150 g isopropanol and filtered through a 10 μm filter. The filtrate was evaporated to dryness and the colorless residue dried overnight under high vacuum. 167.1 g (71%) of a colorless, waxy, chromatographically (UPLC) pure product was obtained.

Example 7

Sodium-2-[poly(oxyethylene)-1,4-dioxybutylene]ethylphosphinate, Mw 500-700 g/mol.

In a glass reactor with mechanical agitator, thermometer and dropping funnel, 212 g (2 mol) sodium hypophosphite monohydrate, dissolved in 600 g water, were placed and heated to 70° C. Then to this solution was added dropwise at 70-72° C. over 90 minutes a solution of 200 g (approx. 0.4 mol) poly(oxyethylene)-1,4-dioxybutylene vinyl ether of molecular weight approx. 500 g/mol and 2 g (0.008 mol) sodium peroxodisulfate in 100 g water.

The reaction was continued for an additional 30 minutes at 70° C. until vinyl ether was no longer detectable by liquid chromatography, and then the reaction solution was evaporated to dryness on a rotary evaporator. The residue was taken up in 600 g isopropanol and this slurry was agitated for 30 minutes at room temperature and then filtered over a filter funnel. The filter cake, mainly consisting of excess sodium hypophosphite, was now washed with 80 mL isopropanol and the combined filtrates dried over 75 g anhydrous sodium sulfate. The dried filtrate was filtered through a pleated filter and evaporated to dryness. 189.4 g crude product was obtained.

For further purification, the highly hygroscopic crude product was dried for two hours under high vacuum and then dissolved in 150 g isopropanol and filtered through a 10 μm filter. The filtrate was evaporated to dryness and the colorless residue dried overnight under high vacuum. 174 g (74%) of a colorless, waxy, chromatographically (UPLC) pure product was obtained.

Example 8

Producing an addition product by addition of sodium phosphinate to di-[methyl-poly(oxyethylene)]maleate (degree of alkoxylation: approx. 22 EO, Mw 1200-1300 g/mol)

In a glass reactor with mechanical agitator, thermometer and dropping funnel, 43.2 g (0.4 mol) sodium hypophosphite monohydrate, dissolved in 300 g water, were placed and heated to 65° C. Then a solution of 228 g (0.2 mol) di-[methyl-poly(oxyethylene)]maleate (degree of alkoxylation: approx. 22 EO) and 2.0 g (0.009 mol) sodium peroxodisulfate in 150 g water was added dropwise to this solution over 70 minutes, wherein the temperature increased to 73° C. Then reaction was continued for an additional 30 minutes at 70° C. until only traces of maleic acid ester could still be detected by liquid chromatography, and then the reaction solution was evaporated to dryness on a rotary evaporator. The residue was taken up in 500 g isopropanol and this slurry was agitated for 30 minutes at room temperature and then filtered over a filter funnel. The filter cake, mainly consisting of excess sodium hypophosphite, was now washed with 80 mL isopropanol and the combined filtrates dried over 70 g anhydrous sodium sulfate. The dried filtrate was filtered through a pleated filter and evaporated to dryness. 230.6 g crude product was obtained.

For further purification, the highly hygroscopic crude product was dried for two hours under high vacuum and then dissolved in 150 g isopropanol and filtered through a 10 μm filter. The filtrate was evaporated to dryness and the colorless residue dried overnight under high vacuum. 189.1 g (77%) of a colorless, waxy, hygroscopic product was obtained, which still contained about 1.5% non-reactive maleic acid ester, which was able to be detected by UPLC.

Production of polymers by free radical polymerization (Examples 9-12)

The relationship between viscosity and molecular weight is described by the Staudinger-Mark-Houwink equation, which is applicable for all types of dissolved macromolecules. This equation states that the viscosity of a polymer solution is proportional to the mean molecular weight of the dissolved polymer.

Based on this, solutions of polymers, made up of the same monomers in equal concentrations, can be compared directly by measuring the viscosity. The comparison permits a qualitative statement to be made regarding the degree of polymerization of the polymers and thus regarding the activity of the regulator used.

In the examples that follow, polymer solutions were produced with a regulator according to the invention and the same polymer solutions, using sodium phosphite, a very weak molecular weight regulator, and were compared based on their viscosity. The viscosity comparison clearly shows the surprising activity of the molecular weight regulator according to the invention.

Example 9

Producing a copolymer from methacrylic acid and methyl-poly(oxyethylene)-methacrylate (degree of alkoxylation: approx. 22 EO) using sodium-3-[methyl-poly(oxyethylene)-oxy-]propyl phosphinate (degree of alkoxylation: 3-10 EO) according to Example 1 as molecular weight regulator
Input 1:
775 g (approx. 0.5 mol) methyl-poly(oxyethylene) methacrylate (70% in water)
129 g (1.5 mol) methacrylic acid
100 g water
Input 2:
10 g sodium peroxodisulfate
100 g water
Input 3:
114 g (approx. 0.2 mol) sodium-3-[methyl-poly(oxyethylene)]propyl phosphinate (70% in water)
50 g water
In a 3 liter, 4-neck round-bottom flask, equipped with a thermometer, a horseshoe mixer with a cool able agitator seal, a 40-cm bulb condenser and a cool able inlet tube for inputs, with automatic metering devices, 450 g water were placed and heated to 80° C. Then 10% of Input 2 and 10% of Input 3 are placed in the flask. Then Input 1 is added dropwise over 3 hours and Inputs 2 and 3 simultaneously over 190 min under agitation, and the temperature held at 95° C. After the addition of the inputs was complete, the reaction was continued for an additional 30 min at 95° C. until peroxide was no longer detectable, and then the mixture was cooled. A clear, colorless polymer solution with a solids content of 39.6% and a viscosity of 362 mPa·s was obtained.

Example 10

Comparison Example 1

A copolymer was produced in analogy to Example 9, with the difference that instead of the molecular weight regulator according to the invention, an equimolar quantity of sodium phosphite was used.

A clear, colorless polymer solution with a solids content of 39.8% and a viscosity of 811 mPa·s was obtained.

Example 11

Producing a copolymer from polyethylene glycol monovinyl ether, acrylic acid and hydroxypropyl acrylate using sodium-3-[methyl-poly(oxethylene)]propyl phosphinate according to Example 1 as molecular weight regulator
Starting mixture:
300 g water
200 g (0.05 mol) polyethylene glycol-monovinyl ether (monomer 1)
11.4 g (approx. 0.02 mol) sodium-3-[methyl-poly(oxyethylene)-oxy-]propyl-phosphinate
2 g NaOH (50%)
1 g FeSO$_4$.7H$_2$O (10%)
Input 1:
50 g water
7.2 g (0.1 mol) acrylic acid
23.4 g (0.18 mol) hydroxypropyl acrylate
Addition A:
1.2 g Rongalit (Na-formaldehyde sulfoxylate)
10 g water
Addition B:
2.2 g hydrogen peroxide (35%)
10 g water
In a 2-liter 4-neck round-bottom flask, equipped with thermometer, horseshoe mixer with cool able agitator seal, 40 cm bulb condenser and coolable inlet tube for inputs with automatic metering devices, the starting material, which contains the monomer 1 and the regulator, was agitated until the vinyl ether had dissolved completely. Then 29 g Input 1 was added to the starting material and mixed well. Then Addition A is added to Input 1 and mixed. Then Addition B was placed in the agitated starting material and simultaneously, Input 1 containing Addition A was added dropwise to the starting material in 1 in 6.5 minutes. In this process, the temperature increased from 21.3 auf 30.1° C., and after 13 minutes the maximum temperature of 31.7° C. was reached. Now, agitation was continued for an additional 15 minutes until peroxide could no longer be detected. A clear polymer solution with a solids content of 37.9% was obtained. After diluting the polymer solution to a solids content of 10%, a viscosity of 23 mPa·s was measured.

Example 12

Comparison Example 2

Production of a copolymer analogously to Example 11, with the difference that instead of the molecular weight regulator according to the invention, an equimolar quantity of sodium phosphite was used A clear, highly viscous polymer solution was obtained. After diluting the polymer solution to a solids content of 10%, a viscosity of 114 mPa·s was measured.

Example 13

Comparison Example 3

Production of a copolymer analogously to Example 11, with the difference that no molecular weight regulator was used.

The viscosity increased greatly over the course of polymerization. After the reaction was ended, a hydrogel was obtained, which could no longer be diluted.

The invention claimed is:

1. Mono-substituted phosphinic acid of formula (I)

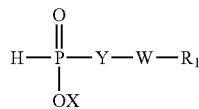
(I)

wherein X is H$^+$, an alkali metal ion, alkaline earth metal ion, divalent or trivalent metal ion, ammonium ion, organic ammonium group or an organic radical with a molecular weight of ≤200 g/mol;

wherein Y represents one of the formulas (II) to (VI)

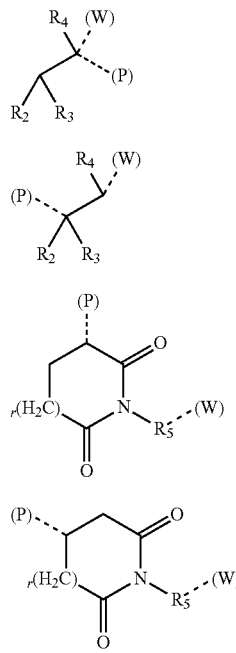

where (P) and (W) correspond to P and W, respectively, in formula (I), wherein W represents one of the formulas (VII) to (X);

(VII)

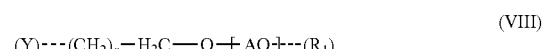
(VIII)

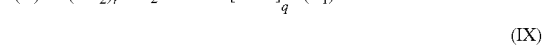
(IX)

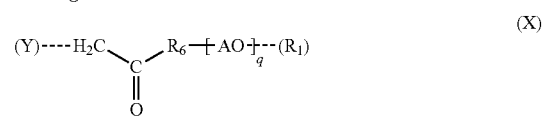
(X)

where (Y) and ($R_1$) correspond to Y and $R_1$, respectively, in formula (I), wherein $R_1$ is H, an alkyl group, an alkylaryl group, or the formula (XI)

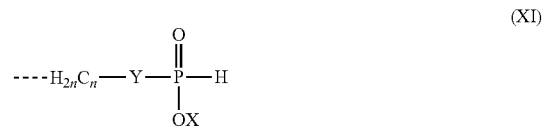
(XI)

wherein the substituent A independently represents a $C_2$- to $C_4$-alkylene group, the subscript q has a value of 2 to 300, the subscript n represents a value of 2 to 4, and the subscript r represents a value of 0 to 1, wherein $R_2$, $R_3$ and $R_4$ independently represent H, $CH_3$, COOH or $CH_2$—COOH, $R_5$ is —$CH_2$—$CH_2$— or —$CH_2$—$CH(CH_3)$ and $R_6$ is O or N.

2. Method for producing a mono-substituted phosphinic acid by reacting a phosphinic acid of formula (XII)

(XII)

with a compound of formula (XIII)

(XIII)

wherein Y' represents a group of formula (III') to (VI')

(III')

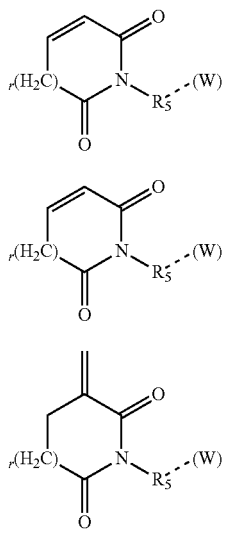

where (W) corresponds to W in formula (XIII),
and wherein W, $R_1$-$R_5$, X and r are radicals and a subscript respectively as described in claim 1, in the presence of a free radical initiator.

3. Method according to claim 2, wherein the phosphinic acid of formula (XII) is sodium phosphinate monohydrate.

4. Method according to claim 2, wherein the method has the following steps:
a) a free radical addition reaction of the phosphinic acid of formula (XII) with a compound of formula (XIII) and a free radical initiator in a solvent;
b) optionally removing the solvent from the reaction mixture and optionally purifying the reaction product from the reaction mixture.

5. Method according to claim 2, wherein the molar ratio of the compound of formula (XIII) to the phosphinic acid of formula (XII) is 1:1 to 1:10.

6. Method according to claim 2, wherein the method includes a solvent that is water or an aqueous solution of a compound selected from the group consisting of ethanol, methanol and isopropanol.

7. A method of regulating molecular weight of a polymer comprising adding the mono-substituted phosphinic acid of claim 1 to monomers in a free radical polymerization reaction.

8. A method of regulating molecular weight of a polymer comprising adding a mono-substitute phosphinic acid produced by the method of claim 2 to monomers in a free radical polymerization reaction.

9. Method for producing polymers P by a free radical polymerization reaction comprising polymerizing monomers M in the presence of a mono-substituted phosphinic acid of formula (I) according to claim 1.

10. Method according to claim 9, wherein the monomers M are selected from the group consisting of:
monoethylenically unsaturated($C_3$-$C_6$)-mono- and dicarboxylic acids,
($C_1$-$C_{20}$)-(meth-)alkyl acrylates, ($C_1$-$C_{20}$)-(meth-)alkyl acrylamides, ($C_1$-$C_{20}$)-(meth-)alkyl acrylonitriles and poly(oxyalkylene)(meth-)acrylates,
vinyl esters of carboxylic acids containing up to 20 C atoms, vinyl aromatics with up to 20 C atoms,
vinyl ethers and allyl ethers of alcohols containing 1 to 12 C atoms, methyl-poly(oxyalkylene)-allyl ethers, or methyl-poly(oxyalkylene) vinyl ethers,
aliphatic hydrocarbons with 2 to 10 C atoms and 1 or 2 olefinic double bonds, cyclic and open-chain N-vinylamides,
and mixtures of these monomers.

11. Method according to claim 9, wherein the free radical polymerization is performed in water.

12. Method according to claim 9, wherein the free radical polymerization is performed in the presence of a solvent including at least one organic solvent and the mono-substituted phosphinic acid has a fraction of ≥70 wt.-% oxypropylene (PO) or oxybutylene groups (BO), based on the molecular weight of the mono-substituted phosphinic acid, wherein the fraction of the organic solvent is 5-90 wt.-%, based on the total weight of the solvent.

13. Method according to claim 9, wherein the free radical polymerization is performed in the presence of a solvent including water and the mono-substituted phosphinic acid has a fraction of ≥50 wt.-% ethylene groups (EO), based on the molecular weight of the mono-substituted phosphinic acid, wherein the fraction of water is 50-100 wt.-%, based on the total weight of the solvent.

14. Method according to claim 9, wherein the polymers P produced by the free radical polymerization have a molecular weight of 500-200.000 g/mol.

15. Polymer of formula (XIV)

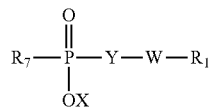

wherein X, Y, W, $R_1$ represent radicals as described in claim 1, and $R_7$ represents a polymer containing at least one monomer M in the polymerized state, selected from the group consisting of:
monoethylenically unsaturated($C_3$-$C_6$)-mono- and dicarboxylic acids,
($C_1$-$C_{20}$)-(meth-) alkyl acrylates, ($C_1$-$C_{20}$)-(meth-)alkyl acrylamides, ($C_1$-$C_{20}$) -(meth-)alkyl acrylonitriles and poly(oxyalkylene)(meth-)acrylates,
vinyl esters of carboxylic acids containing up to 20 C atoms, vinyl aromatics with up to 20 C atoms,
vinyl ethers and allyl ethers of alcohols containing 1 to 12 C atoms, methyl-poly (oxyalkylene)-allyl ethers, or methyl-poly(oxyalkylene) vinyl ethers,
aliphatic hydrocarbons with 2 to 10 C atoms and 1 or 2 olefinic double bonds, cyclic and open-chain N-vinylamides,
and mixtures of these monomers, wherein $R_7$ has a molecular weight of 500-200.000 g/mol.

16. Method for producing polymers P by a free radical polymerization reaction comprising polymerizing monomers M in the presence of a mono-substituted phosphinic acid produced by the method of claim 2.

* * * * *